United States Patent
Puro

(10) Patent No.: US 9,243,059 B2
(45) Date of Patent: *Jan. 26, 2016

(54) HUMANIZED ANTI-N2 ANTIBODIES AND METHODS OF TREATING ISCHEMIA-REPERFUSION INJURY

(71) Applicant: DecImmune Therapeutics, Inc., Cambridge, MA (US)

(72) Inventor: Robyn J. Puro, Brookline, MA (US)

(73) Assignee: DecImmune Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,316

(22) Filed: Mar. 12, 2014

(65) Prior Publication Data

US 2014/0271627 A1    Sep. 18, 2014

Related U.S. Application Data

(60) Provisional application No. 61/777,647, filed on Mar. 12, 2013.

(51) Int. Cl.
*C07K 16/18* (2006.01)
*A61K 39/395* (2006.01)
*A61K 39/00* (2006.01)

(52) U.S. Cl.
CPC ............ *C07K 16/18* (2013.01); *A61K 39/39583* (2013.01); *A61K 2039/505* (2013.01); *C07K 2317/24* (2013.01); *C07K 2317/34* (2013.01); *C07K 2317/92* (2013.01)

(58) Field of Classification Search
CPC ............... C07K 16/18; C07K 2317/24; C07K 2317/34; C07K 2317/92; A61K 2039/505
See application file for complete search history.

(56) References Cited

U.S. PATENT DOCUMENTS

| | | | |
|---|---|---|---|
| 5,859,205 | A | 1/1999 | Adair et al. |
| 5,928,893 | A | 7/1999 | Kang et al. |
| 6,753,314 | B1 | 6/2004 | Giot et al. |
| 7,442,783 | B2 | 10/2008 | Carroll et al. |
| 7,863,419 | B2 | 1/2011 | Taylor et al. |
| 8,324,352 | B2 | 12/2012 | Carroll |
| 9,067,983 | B2 | 6/2015 | Carroll |
| 2003/0099656 | A1 | 5/2003 | Patti et al. |
| 2003/0202975 | A1 | 10/2003 | Tedder |
| 2004/0006208 | A1 | 1/2004 | Karpusas et al. |
| 2004/0131607 | A1 | 7/2004 | Carroll et al. |
| 2004/0214272 | A1 | 10/2004 | Larosa et al. |
| 2005/0276811 | A1 | 12/2005 | Carroll et al. |
| 2006/0024296 | A1 | 2/2006 | Williams et al. |
| 2007/0071675 | A1 | 3/2007 | Wu et al. |
| 2007/0135998 | A1 | 6/2007 | Van Vlijmen et al. |
| 2007/0280881 | A1 | 12/2007 | Braslawsky et al. |
| 2008/0260731 | A1 | 10/2008 | Bernett et al. |
| 2008/0262203 | A1 | 10/2008 | Clegg et al. |
| 2009/0176966 | A1 | 7/2009 | Carroll et al. |
| 2009/0299038 | A1 | 12/2009 | Nakamura et al. |
| 2010/0136684 | A1 | 6/2010 | Carroll et al. |
| 2010/0272723 | A1 | 10/2010 | Bernett et al. |
| 2011/0098448 | A1 | 4/2011 | Korth et al. |
| 2012/0082664 | A1 | 4/2012 | Bernett et al. |
| 2012/0093835 | A1 | 4/2012 | Carroll |
| 2014/0056871 | A1 | 2/2014 | Carroll |

FOREIGN PATENT DOCUMENTS

| | | |
|---|---|---|
| WO | 9108756 A1 | 6/1991 |
| WO | 9636360 A1 | 11/1996 |
| WO | 0018437 A1 | 4/2000 |
| WO | 0032825 A2 | 6/2000 |
| WO | 0164835 A2 | 9/2001 |
| WO | 0175067 A2 | 10/2001 |
| WO | 0188088 A2 | 11/2001 |
| WO | 0193982 A1 | 12/2001 |
| WO | 03055982 A2 | 7/2003 |
| WO | 2004002210 A2 | 1/2004 |
| WO | 2005085288 A2 | 9/2005 |
| WO | 2011071883 A1 | 6/2011 |

OTHER PUBLICATIONS

Paul, WE. Fundamental Immunology, 3rd ed. Raven Press, NY, Chap. 9, pp. 292-295, 1993.*
Colman, PM. Research in Immunology, Elsevier, NY, 145(1):33-36, 1994.*
Database EMBL [Online], "*Mus musculus* VH9D5 mRNA for anti-dsRNA (RDV-RNA) antibody, partial cds.", retrieved from EBI accession No. EM STD:AB050071, Database accession No. AB050071, Apr. 2, 2002.
*Mus Musculus* Myosin Heavy Chain IX (Myh9), mRNA. [online]. [retrieved on Feb. 23, 2015]. GenBank Accession No. NM-022410.
Rudikoff, et al., "Single Amino Acid Substitution Altering Antigen-Binding Specificity," Proc Natl Acad Sci USA 79:1979-1983; Mar. 15, 1982.
Austen, et al., "Self-Reactive Immunoglobulin M from Peritoneal B Cells Mediates Murine Intestinal Ischemia-Reperfusion Injury." Surgical Forum, 1998, vol. 49, pags 341-342.
Carroll, M.O., "The Role of Complement and Complement Receptors in Induction and Regulation of Immunity." Ann. Rev. Immunol. (1998) 16, 545-568.
Padlan, "Anatomy of the antibody molecule" Molecular Immun. 31 (3) (1994), pp. 169-217.
Hechtman, et al., "Intestinal Ischemia-Reperfusion Injury is Mediated by Natural Antibody derived from Peritoneal Bl-a Cells." FASEB Journal. 1998, vol. 12, p. A34.
Klimka, et al., "Human anti-CD30 recombinant antibodies by guided phage antibody selection using cell panning" British Journal of Cancer (2000) 83: pp. 252-260.

(Continued)

*Primary Examiner* — Robert Landsman
(74) *Attorney, Agent, or Firm* — Mahreen Chaudhry Hoda; Carolyn S. Elmore; Elmore Patent Law Group, P.C.

(57) ABSTRACT

The present invention encompasses humanized antibodies that specifically bind N2 peptide, methods for the preparation thereof and methods for the use thereof.

35 Claims, 1 Drawing Sheet

(56) References Cited

OTHER PUBLICATIONS

Williams, et al., "Intestinal Reperfusion Injury is Mediated by IgM and Complement," J appl. Physiol, 86:938-42 (1999).
"*Aspergillus nidulans* FGSC A4 chromosome I ANcontig1.116, whole genome shotgun sequence," GenBank Accession No. AACD01000116.1, retrieved on Feb. 23, 2015.
Weiser, et al., "Reperfusion Injury of Ischemic Skeletal Muscle is Mediated by Natural Antibody and Complement." Journal Experimental Medicine. 1996, vol. 183, pp. 2343-2348.
"*Xenopus laevis* hypothetical protein LOC398719, mRNA (cDNA clone Image:4889191), partial cds," GenBank accession No. BC057729), retrieved on Feb. 23, 2015.
"*Arabidopsis thaliana* transcribed RNA for snRNA_08920, complete sequence, ecotype: Col-0," GenBank Accession No. AB957589, retrieved on Feb. 23, 2015.
Zhang, Ming, et al, "Activation of the Lectin Pathway by Natural IgM in a Model of Ischemia/Reperfusion Injury," Journal of Immunology, 177:4272-4734 (2006).
Chan, R.K, et al., "Attenuation of skeletal muscle reperfusion injury with intravenous 12 amino acid peptides that bind to pathogenic IgM," Surgery, pp. 1-8 (2006).
Ahmadi-Yazdi, C., et al., "Attenuation of the Effects of Rat Hemorrhagic Shock with a Reperfusion Injury-Inhibiting Agent Specific to Mice," Shock, 32(3):295-301 (2009).
Haas, M.S. et al. "Blockade of self-reactive IgM significantly reduces injury in a murine model of acute myocardial infarction," Cardiovascular Research, 87:618-627 (2010).
Hofmann, U., et al., "Nothing but natural: targeting natural IgM in ischaemia/reperfusion injury," Cardiovascular Research, 87:589-590 (2010).
Tatlidede, S.H., et al., "Improved Survival of Murine Island Skin Flaps by Prevention of Reperfusion Injury," Plast. Reconstr. Surg., 123(5):1431-1439 (2009).
Suber, F., et al., "Innate response to self-antigen significantly exacerbates burn wound depth," PNAS, 104 (10):3973-3977 (2007).
Huang, J., et al., "Neuronal Protection in Stroke by an sLex-Glycosylated Complement Inhibitory Protein," Science, 285:595-599 (1999).
Zhang, M., et al., "The role of natural IgM in myocardial ischemia-reperfusion injury," J. of Molecular and Cellular Cardiology, 41:62-67 (2006).
Zhang, M, et al., "Identification of the target self-antigens in reperfusion injury," JEM, www.jem.org/cgi/doi/10.1084/jem.20050390, pp. 1-12 (2006).
Yu, et al., "Modulation of Natural IgM Binding and Complement Activation by Natural IgG Antibodies," J. Immunol., 157, pp. 5163-5168, 1996.
"*Homo sapiens* myosin, heavy chain 9, non-muscle, mRNA (cDNA clone Image:5563109), partial cds"; (GenBank accession No. BC049849, retrieved on Feb. 23, 2015).
Beiboer, et al., "Guided selection of a pan carcinoma specific antibody reveals similar binding characteristics yet structural divergence between the original murine antibody and its human equivalent" J. Mol Biol. (2000) 296: pp. 833-849.
Austen, et al., "Murine Hindlimb Reperfusion Injury Can Be Initiated by a Self-Reactive Monoclonal IgM," Surgery, C30 136(2):401-406, (2004).
"*Homo sapiens* mRNA; cDNA DKFZp451 J0218 (from clone DKFZp451 J0218); complete cds" (GenBank accession No. AL832639, retrieved on Feb. 23, 2015).
"*Arabidopsis thaliana* unknown protein (At3g57990) mRNA, complete cds," GenBank Accession No. AY122933, retrieved on Feb. 23, 2015.
William, E. Paul, M. D. "Fundamental Immunology" 3rd Edition, 1993, 292-295.
Zhang, et al. "Identification of a Peptide Inhibitor of Ischemia/Reperfusion Injury," Molecular Immunology, vol. 41, p. 331 (282), Jun. 2004.
Zhang, et al., Identification of a Specific Self-Reactive IgM Antibody that Initiates Intestinal Ischemia/Reperfusion Injury, PNAS USA 101:3886-91, 2004.
Guo, et al., "Protein Tolerance to Random Amino Acid Change," Proc. Natl. Acad. Sci., 101(25): 9205-10, (2004).
"Nonmuscle Myosin Heavy chain B," (GenBnk accession No. Q27989, retrieved on Feb. 23, 2015).
"*Bos taurus* nonmuscle myosin heavy chain B mRNA fragment II, partial cds", (GenBank acccession No. U15693, retrieved on Feb. 23, 2015).
"*Oryctolagus curriculus* mRNA for myosin heavy chain, partial cds", (rGenBank accession No. D63694, retrieved on Feb. 23, 2015).
Restriction Requirement, U.S. Appl. No. 14/206,368, dated Oct. 24, 2014.
Non-Final Office Action, U.S. Appl. No. 14/206,368, dated Jun. 30, 2015.
Pending U.S. Appl. No. 14/726,016, filed May 29, 2015.
Co-pending U.S. Appl. No. 14/206,368, filed Mar. 12, 2014.

* cited by examiner

Sequence comparison of m21G6 and humanized derivatives m21G6
QVQLQQPGAELVKPGASVKLSCKASGY TSYYMYW VK RPGQG EW I GINPSNGGTNFNEKF SKAT T D SSSTAYMQLSLTSEDSAVY CTRWGYDREW FAY WGQGTLVTVSA

H1-21G6 VH (21/28)
QVQLVQSGAEVKPGASVKLSCKASGY FTSYYMYWVKQAPGQGLEW I GGINPSNGGTNFNEK FKSKAT LTVDKSASTAYMELSSLRSEDTAVY CTRWGYDRE WFAYWGQGTLVTVSS

H2-21G6 VH (Germline HuIgH1-
QVQLVQSGAEVKKPGASVKVSCKASGY TF SYYM WVRQAPGQGLEW GGINPSNGGTNFNEK KSKATMTVDKSTSTAYMELRSLRSDDSAVY CTRWGYDREW FAYWGQGTLVTVSS

H3-21G6 VH (Germline HuIgH1-
QVQLVQSGAEVKKPGSSVKVSCKASGY TF TSYYMYWVRQAPGQGLEW I GGINPSNGGTNFNE FKSKATITVDKSTSTAVMELSSLRSEDTAVY CTRWGYDREV FAYWGQGTLVTVSS m21G6
DIV ITQAAPSVPVTPGESVSIS CRSSKSLLHSNGNTY YW LQRPGQSPQ RMSN ASGVPDRFS S T A TLRISRVEAEDVG VYYCMQHLE YPFT GSGTKLEIKR

L1-21G6 VL (PopVk,
DIVMTQSPATLSVSPGERATIS CRSSKSLLHSNGNTY YWFQQKPGQPPKV LIYRMSN ASGVPARFSGSGSGTDFLTISS VEPED FATYYCMQH EYPFTFGGGTKLEIKR

L2-21G6 VL (Germline HuIgKV2-
DIVMTQSPLSLPVTPGEPASIS CRSSKSLLHSNGNTY YWFLQKPGQSPQL LIYRMSN ASGVPDRFSGSGSGTDFTLKISRVEAEDVG YYCMQHLE PFTFGQGTKLEIKR

L3-21G6 VL (Germline HuIgKV2-
DIVMTQTPLSLSYTPGQPASIS CRSSKSLLHSNGNTY YWFLQKPGQSPQL LIYRMSN ASGVPDRFSGSGSGTDFTLKISRVEAEDVG YYCMQHLE YPFTFGQGTKLEIKR Bold = amino acid differences between germline sequence and parental m21g6
Silver vernier zones
Boxes indicates CDR regions

HUMANIZED ANTI-N2 ANTIBODIES AND METHODS OF TREATING ISCHEMIA-REPERFUSION INJURY

RELATED APPLICATION

This application claims the benefit of U.S. Provisional Application No. 61/777,647, filed on Mar. 12, 2013. The entire teachings of the above application(s) are incorporated herein by reference.

GOVERNMENT SUPPORT

The invention was supported, in whole or in part, by Grant No. 10388353 from the National Institutes of Health. The Government has certain rights in the invention.

BACKGROUND OF THE INVENTION

It has been demonstrated that ischemia-reperfusion injury can be initiated by clonally-specific pathogenic IgM that activates the classical pathway of complement (Zhang et al. (2004) Proc. Natl. Acad. Sci. 101(11):3886-3891). Pathogenic IgM (also referred to as "natural IgM") recognizes and binds to a self-antigen which is an antigen expressed or exposed on damaged tissue, for example, on damaged ischemic tissue. Binding of pathogenic IgM to the self-antigen initiates inflammation by activating complement in the classical pathway. U.S. Pat. No. 7,442,783 describes the major epitope for binding of natural IgMs as a conserved region within type II non-muscle myosin heavy chain (NMHC) proteins. This epitope is referred to as the N2 12-mer peptide.

Inhibitors of the interaction between the N2 epitope and pathogenic IgM have been described as useful for the treatment of inflammatory diseases and conditions, including ischemia/reperfusion injury. For example, U.S. Pat. No. 8,324,352 describes the murine monoclonal antibody referred to as 21G6. Murine 21G6 (m21G6) was shown to bind to the N2 peptide and provide protection against ischemia/reperfusion injury in animal models. It would be advantageous to develop additional therapeutic agents that bind the N2 peptide and that can be used for treating inflammatory conditions such as ischemia/reperfusion injury.

SUMMARY OF THE INVENTION

The present invention encompasses humanized derivatives of the murine 21G6 antibody that specifically bind N2 peptide. As shown in the Examples below, humanized antibodies have been developed that bind the N2 peptide.

In one embodiment, the invention is directed to an antibody or antigen binding fragment thereof comprising framework regions from a human immunoglobulin and comprising the variable heavy chain (VH) complementarity determining regions (CDRs) of the murine 21G6 antibody and the variable light chain (VL) CDRs of the murine 21G6 antibody.

In some embodiments, the invention is directed to a humanized, anti-N2 antibody or antigen-binding fragment thereof comprising a heavy chain variable (VH) region and a light chain variable (VL) region, wherein:
  i. the VH region comprises three complementarity determining regions (CDRs) VH CDR1, VH CDR2 and VH CDR3 wherein the VH CDR1 comprises SEQ ID NO: 3, VH CDR2 comprises SEQ ID NO: 4 and VH CDR3 comprises SEQ ID NO: 5;
  ii. the VH region comprises four framework regions (FWR) VH FWR1, VH FWR2, VH FWR3 and VH FWR4 wherein:
    a. the VH FWR1 comprises SEQ ID NO: 15, SEQ ID NO: 19 or SEQ ID NO: 23;
    b. The VH FWR2 comprises SEQ ID NO: 16, SEQ ID NO: 20 or SEQ ID NO:24;
    c. VH FWR3 comprises SEQ ID NO: 17, SEQ ID NO: 21, SEQ ID NO: 25, SEQ ID NO: 43, SEQ ID NO: 44 or SEQ ID NO: 45; and
    d. VH FWR4 comprises SEQ ID NO: 18, SEQ ID NO: 22, or SEQ ID NO: 26;
  iii. the VL region comprises three complementarity determining regions (CDRs) VL CDR1, VL CDR2 and VL CDR3 wherein the VL CDR1 comprises SEQ ID NO: 6, VH CDR2 comprises SEQ ID NO: 7 and VH CDR3 comprises SEQ ID NO: 8;
  iv. the VL region comprises four framework regions (FWR) VL FWR1, VL FWR2, VL FWR3 and VL FWR4 wherein:
    a. the VL FWR1 comprises SEQ ID NO: 27, SEQ ID NO: 31, or SEQ ID NO: 35;
    b. VL FWR2 comprises SEQ ID NO: 28, SEQ ID NO: 32, or SEQ ID NO: 36;
    c. VL FWR3 comprises SEQ ID NO: 29, SEQ ID NO: 33, or SEQ ID NO: 37; and
    d. VL FWR4 comprises SEQ ID NO: 30, SEQ ID NO: 34, or SEQ ID NO: 38.

In certain additional embodiments, the antibody or antigen-binding fragment has a VH region that comprises a sequence selected from the group consisting of SEQ ID NO: 9, SEQ ID NO: 10 and SEQ ID NO: 11.

In additional aspects, the antibody or antigen-binding fragment has a VL region that comprises a sequence selected from the group consisting of SEQ ID NO: 12, SEQ ID NO: 13 and SEQ ID NO: 14.

In yet additional aspects, the antibody or antigen-binding fragment has a VH region that consists of SEQ ID NO: 9 and has a VL region that consists of SEQ ID NO: 12. In other embodiments, the antibody or antigen-binding fragment has a VH region that consists of SEQ ID NO: 9 and has a VL region that consists of SEQ ID NO: 13. In another aspect, the antibody or antigen-binding fragment has a VH region that consists of SEQ ID NO: 9 and the VL region consists of SEQ ID NO: 14. In a further embodiment, the antibody or antigen-binding fragment has a VH region that consists of SEQ ID NO: 10 and has a VL region consists of SEQ ID NO: 12. In certain additional aspects, the antibody or antigen-binding fragment has a VH region that consists of SEQ ID NO: 10 and has a VL region that consists of SEQ ID NO: 13. In an additional embodiment, the antibody or antigen-binding fragment has a VH region that consists of SEQ ID NO: 10 and has a VL region that consists of SEQ ID NO: 14. In another aspect of the invention, the antibody or antigen-binding fragment of has a VH region that consists of SEQ ID NO: 11 and a VL region that consists of SEQ ID NO: 12. In another embodiment, the antibody or antigen-binding fragment has a VH region that consists of SEQ ID NO: 11 and a VL region that consists of SEQ ID NO: 13. In another embodiment, the antibody or antigen-binding fragment has a VH region that consists of SEQ ID NO: 11 and a VL region that consists of SEQ ID NO: 14.

In some embodiments, the antibody or antigen-binding fragment has a VH region that consists of SEQ ID NO: 43 and a VL region that consists of a sequence selected from the group consisting of SEQ ID NO: 12, SEQ ID NO: 13 and SEQ ID NO: 14. In additional embodiments, the antibody or antigen-binding fragment has a VH region that consists of SEQ ID NO: 44 and a VL region that consists of a sequence selected from the group consisting of SEQ ID NO: 12, SEQ ID NO: 13 and SEQ ID NO: 14. In yet other embodiments, the antibody or antigen-binding fragment has a VH region that consists of SEQ ID NO: 45 and a VL region that consists of a sequence selected from the group consisting of SEQ ID NO: 12, SEQ ID NO: 13 and SEQ ID NO: 14. In another aspect, the invention is an antibody or antigen-binding fragment has a VH region consists of SEQ ID NO: 42 and VL region consists of a sequence selected from the group consisting of SEQ ID NO: 12, SEQ ID NO: 13 and SEQ ID NO: 14.

In yet additional embodiments, the invention is directed to a humanized, anti-N2 antibody or antigen-binding fragment thereof comprising a heavy chain variable (VH) region comprising a sequence selected from the group consisting of SEQ ID NO: 9, SEQ ID NO: 10 and SEQ ID NO: 11.

In a further embodiment, the invention is a humanized, anti-N2 antibody or antigen-binding fragment thereof, comprising a light chain variable (VL) region comprising a sequence selected from the group consisting of SEQ ID NO: 12, SEQ ID NO: 13 and SEQ ID NO: 14.

BRIEF DESCRIPTION OF THE DRAWING

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The FIGURE shows a sequence comparison of the murine 21G6 heavy chain variable (VH) region (SEQ ID NO: 1) and the humanized heavy chain variable regions (VH) H1, H2 and H3 (SEQ ID NOs: 9, 10 and 11, respectively) and also shows a sequence comparison of the murine 21G6 light chain variable (VL) region (SEQ ID NO: 2) and the humanized light chain variable regions light chain (VL) regions L1, L2 and L3 (SEQ ID NOs: 12, 13, and 14, respectively). The CDR regions are indicated by the boxes.

DETAILED DESCRIPTION OF THE INVENTION

A description of preferred embodiments of the invention follows.

The words "a" or "an" are meant to encompass one or more, unless otherwise specified.

An "antibody" is a binding molecule including immunoglobulin molecules, antibody fragments, and immunologically active portions of immunoglobulin molecules, for example, molecules that contain an antigen-binding site. Native antibodies and immunoglobulins are usually heterotetrameric glycoproteins of about 150,000 daltons, composed of two identical light chains and two identical heavy chains. Each heavy chain has at one end a variable domain followed by a number of constant domains. Each light chain has a variable domain at one end and a constant domain at its other end. An antibody binds specifically to an antigen (or other molecule) if the antibody binds preferentially to the antigen, and, for example, has less than about 30%, preferably less than about 20%, less than about 10%, or less than about 1% cross-reactivity with another molecule. The terms "antibody" and "immunoglobulin" are used interchangeably.

"Bind" or "binding" are used herein to refer to detectable relationships or associations (e.g. biochemical interactions) between molecules.

An "isolated" molecule, for example, an isolated antibody or isolated peptide, refers to a condition of being separate or purified from other molecules present in the natural environment or as they occur in nature.

The N2 epitope is an epitope of the self-antigen, the 12 amino acid sequence expressed in non-muscle myosin heavy chain (NMHC) type II. The 12-amino acid sequence is LMKNMDPLNDNV (SEQ ID NO: 47). The N2 epitope is described in detail in U.S. Pat. No. 7,442,783, the contents of which are expressly incorporated by reference herein. "Natural IgM" or "pathogenic IgM" refers to an IgM antibody that is naturally produced in a mammal (for example, a human) that binds to the N2 epitope and initiates inflammation by activating complement in the classical pathway.

In some embodiments, antibody or antigen-binding fragment thereof binds to SEQ ID NO: 47. In additional embodiments, the antibody or antigen-binding fragment thereof binds to an epitope wherein the amino acid sequence of the epitope has at least about 80%, 85%, 90%, 95%, or 98% sequence identity to the amino acid sequence of SEQ ID NO: 47. In certain embodiments, the epitope comprises the amino acid sequence LMKNMDPLNDNI (SEQ ID NO: 48).

The hypervariable region of an antibody or fragment thereof refers to the amino acid residues that contribute to antigen-binding. The hypervariable region comprises amino acid residues from the complementarity determining regions (CDRs). The CDRs are specific regions within variable regions of the heavy and the light chain. Generally, the variable region consists of four framework regions (FWR1, FWR2, FWR3, FWR4) and three CDRs arranged as follows: NH$_2$-FWR1-CDR1-FWR2-CDR2-FWR3-CDR3-FWR4-constant region-C(O)OH. The term "framework regions" refers to those variable domain amino acid residues other than the CDR residues and include, for example, FWR1, FWR2, FWR3, and FWR4.

As described above, the present invention is directed to humanized derivatives of the murine 21G6 antibody described in U.S. Pat. No. 8,324,352, the contents of which are expressly incorporated herein. In certain embodiments, the humanized antibodies and fragments thereof bind the N2 peptide. The amino acid sequences of the heavy chain variable region (VH) and the light chain variable region (VL) of the murine 21G6 antibody are shown in The FIGURE and are below as SEQ ID NOs: 1 and 2:

```
Murine 21G6 (m21G6) VH
                                           (SEQ ID NO: 1)
QVQLQQPGAELVKPGASVKLSCKASGYTFTSYYMYWVKQRPGQGLEWIGG

INPSNGGTNFNEKFKSKATLTVDKSSSTAYMQLSSLTSEDSAVYYCTRWG

YDREWFAYWGQGTLVTVSA.

Murine 21G6 VL
                                           (SEQ ID NO: 2)
DIVMTQAAPSVPVTPGESVSISCRSSKSLLHSNGNTYLYWFLQRPGQSPQ

VLIYRMSNLASGVPDRFSGSGSGTAFTLRISRVEAEDVGVYYCMQHLEYP

FTFGSGTKLEIKR.
```

The underlined amino acids represent the complementarity determining regions.

The FIGURE shows the amino acid sequences of three VH regions encompassed by the invention: H1-21G6, H2-21G6 and H3-21G6. The amino acid sequences of the H1-21G6, H2-21G6 and H3-21G6 VH regions are SEQ ID NOs: 9, 10 and 11, respectively:

H1-21G6 VH
(SEQ ID NO: 9)
QVQLVQSGAEVVKPGASVKLSCKASGYTFT<u>SYYMY</u>WVKQAPGQGLEWIG<u>G</u>

<u>INPSNGGTNFNEKFKS</u>KATLTVDKSASTAYMELSSLRSEDTAVYYCTRW<u>G</u>

<u>YDREWFAY</u>WGQGTLVTVSS.

H2-21G6 VH
(SEQ ID NO: 10)
QVQLVQSGAEVKKPGASVKVSCKASGYTFT<u>SYYMY</u>WVRQAPGQGLEWIG<u>G</u>

<u>INPSNGGTNFNEKFKS</u>KATMTVDKSTSTAYMELRSLRSDDSAVYYCTRW<u>G</u>

<u>YDREWFAY</u>WGQGTLVTVSS.

H3-21G6 VH
(SEQ ID NO: 11)
QVQLVQSGAEVKKPGSSVKVSCKASGYTFT<u>SYYMY</u>WVRQAPGQGLEWIG<u>G</u>

<u>INPSNGGTNFNEKFKS</u>KATITVDKSTSTAYMELSSLRSEDTAVYYCTRW<u>G</u>

<u>YDREWFAY</u>WGQGTLVTVSS.

The underlined amino acids represent the complementarity determining regions.

The FIGURE also shows the amino acid sequences of three VL regions encompassed by the invention: L1-21G6, L2-21G6 and L3-21G6. The amino acid sequences of L1-21G6, L2-21G6 and L3-21G6 VH regions are SEQ ID NOs: 12, 13 and 14, respectively.

L1-21G6 VL
(SEQ ID NO: 12)
DIVMTQSPATLSVSPGERATISC<u>RSSKSLLHSNGNTYLY</u>WFQQKPGQPPK

VLIY<u>RMSNLAS</u>GVPARFSGSGSGTDFTLTISSVEPEDFATYYC<u>MQHLEYP</u>

<u>FT</u>FGGGTKLEIKR.

L2-21G6 VL
(SEQ ID NO: 13)
DIVMTQSPLSLPVTPGEPASISC<u>RSSKSLLHSNGNTYLY</u>WFLQKPGQSPQ

LLIY<u>RMSNLAS</u>GVPDRFSGSGSGTDFTLKISRVEAEDVGVYYC<u>MQHLEYP</u>

<u>FT</u>FGQGTKLEIKR.

L3-m21G6 VL
(SEQ ID NO: 14)
DIVMTQTPLSLSYTPGQPASISC<u>RSSKSLLHSNGNTYLY</u>WFLQKPGQSPQ

LLIY<u>RMSNLAS</u>GVPDRFSGSGSGTDFTLKISRVEAEDVGVYYC<u>MQHLEYP</u>

<u>FT</u>FGQGTKLEIKR.

The underlined amino acids represent the complementarity determining regions.

The names "H1-21G6," "H2-21G6" and "H3-21G6" are used interchangeably herein with "H1," "H2" and "H3," respectively. The names "L1-21G6," "L2-21G6" and "L3-21G6" are used interchangeably with "L1," "L2" and "L3," respectively.

CDR1, CDR2 and CDR3 of the VH regions of the antibodies or fragments of the present invention are SYYMY (SEQ ID NO: 3), GINPSNGGTNFNEKFKS (SEQ ID NO: 4), GYDREWFAY (SEQ ID NO: 5), respectively. CDR1, CDR2 and CDR3 of the VL regions of the antibodies or fragments of the present invention are RSSKSLLHSNGNTYLY (SEQ ID NO: 6), RMSNLAS (SEQ ID NO: 7), and MQHLEYPFT (SEQ ID NO: 8), respectively. The VL region of the antibody or antigen-binding fragments of the present invention includes at least two of the CDRs of m21G6 VL. The VH region of the antibody or antigen-binding fragment of the invention includes at least two CDRs of the m21G6 VH. In some embodiments, the humanized antibodies include all three CDRs of m21G6 VH and/or all three CDRs of the m21G6 VL. The framework regions FWR1, FWR2, FWR3 and FWR4 of the VH region of each of H1-21G6, H2-21G6 and H3-21G6 are shown below:

H1 VH FWR1
QVQLVQSGAEVVKPGASVKLSCKASGYTFT.    (SEQ ID NO: 15)

H1 VH FWR2
WVKQAPGQGLEWIG.                    (SEQ ID NO: 16)

H1 VH FWR3
KATLTVDKSASTAYMELSSLRSEDTAVYYCTR.  (SEQ ID NO: 17)

H1 VH FWR4
WGQGTLVTVSS.                       (SEQ ID NO: 18)

H2 VH FWR1
QVQLVQSGAEVKKPGASVKVSCKASGYTFT.    (SEQ ID NO: 19)

H2 VH FWR2
WVRQAPGQGLEWIG.                    (SEQ ID NO: 20)

H2 VH FWR3
KATMTVDKSTSTAYMELRSLRSDDSAVYYCTR.  (SEQ ID NO: 21)

H2 VH FWR4
WGQGTLVTVSS.                       (SEQ ID NO: 22)

H3 VH FWR1
QVQLVQSGAEVKKPGSSVKVSCKASGYTFT.    (SEQ ID NO: 23)

H3 VH FWR2
WVRQAPGQGLEWIG.                    (SEQ ID NO: 24)

H3 VH FWR3
KATITVDKSTSTAYMELSSLRSEDTAVYYCTR.  (SEQ ID NO: 25)

H3 VH FWR4
WGQGTLVTVSS.                       (SEQ ID NO: 26)

The framework regions FWR1, FWR2, FWR3 and FWR4 of each of the VL region of each of L1-21G6, L2-21G6 and L3-21G6 are shown below:

L1 VL FWR1
DIVMTQSPATLSVSPGERATISC.           (SEQ ID NO: 27)

L1 VL FWR2
WFQQKPGQPPKVLIY.                   (SEQ ID NO: 28)

L1 VL FWR3
GVPARFSGSGSGTDFTLTISSVEPEDFATYYC.  (SEQ ID NO: 29)

L1 VL FWR4
FGGGTKLEIKR.                       (SEQ ID NO: 30)

L2 VL FWR1
DIVMTQSPLSLPVTPGEPASISC.           (SEQ ID NO: 31)

L2 VL FWR2
WFLQKPGQSPQLLIY.                   (SEQ ID NO: 32)

L2 VL FWR3
GVPDRFSGSGSGTDFTLKISRVEAEDVGVYYC.  (SEQ ID NO: 33)

L2 VL FWR4
FGQGTKLEIKR.                       (SEQ ID NO: 34)

L3 VL FWR1
DIVMTQTPLSLSYTPGQPASISC.           (SEQ ID NO: 35)

-continued

```
L3 VL FWR2
WFLQKPGQSPQLLIY.                (SEQ ID NO: 36)

L3 VL FWR3
GVPDRFSGSGSGTDFTLKISRVEAEDVGVYYC. (SEQ ID NO: 37)

L3 VL FWR4
FGQGTKLEIKR.                    (SEQ ID NO: 38)
```

As described above, the present invention encompasses an antibody or antigen-binding fragment thereof comprising VH CDR1, CDR2 and CDR3 having the amino acid sequences SEQ ID NO: 3, SEQ ID NO: 4 and SEQ ID NO: 5, respectively, and VL CDR1, CDR2 and CDR3 having the amino acid sequences SEQ ID NO: 6, SEQ ID NO: 7 and SEQ ID NO: 8, respectively, and further comprising a VH region that comprises four framework regions (FWR) VH FWR1, VH FWR2, VH FWR3 and VH FWR4 wherein:
  a. the VH FWR1 comprises SEQ ID NO: 15, SEQ ID NO: 19 or SEQ ID NO: 23;
  b. The VH FWR2 comprises SEQ ID NO: 16, SEQ ID NO: 20 or SEQ ID NO:24;
  c. VH FWR3 comprises SEQ ID NO: 17, SEQ ID NO: 21, SEQ ID NO: 25, SEQ ID NO: 43, SEQ ID NO: 44 or SEQ ID NO: 45; and
  d. VH FWR4 comprises SEQ ID NO: 18, SEQ ID NO: 22, or SEQ ID NO: 26;
and a VL region that comprises four framework regions (FWR) VL FWR1, VL FWR2, VL FWR3 and VL FWR4 wherein:
  a. the VL FWR1 comprises SEQ ID NO: 27, SEQ ID NO: 31, or SEQ ID NO: 35;
  b. VL FWR2 comprises SEQ ID NO: 28, SEQ ID NO: 32, or SEQ ID NO: 36;
  c. VL FWR3 comprises SEQ ID NO: 29, SEQ ID NO: 33, or SEQ ID NO: 37; and
  d. VL FWR4 comprises SEQ ID NO: 30, SEQ ID NO: 34, or SEQ ID NO: 38.

The terms "comprises" and "comprising" permits (but does not require) the inclusion of additional elements. For example, in the context of an amino acid sequence, the terms "comprises" and "comprising" permits the inclusion of additional amino acids at either the N-terminus and/or the carboxy terminal end. In some embodiments, the framework region of the VH and VL regions comprise a specific indicated amino acid sequence and one to three additional amino acids at the N-terminus and/or at the carboxy terminal end.

In certain additional aspects, the antibody or antigen binding fragment of the invention comprises a heavy chain variable (VH) region and a light chain variable (VL) region, wherein
  i. the VH comprises three complementarity determining regions (CDRs) VH CDR1, VH CDR2 and VH CDR3 wherein the VH CDR1 consists of SEQ ID NO:3, VH CDR2 consists of SEQ ID NO: 4 and VH CDR3 consists of SEQ ID NO: 5;
  ii. the VH region comprises four framework regions (FWR) VH FWR1, VH FWR2, VH FWR3 and VH FWR4 wherein:
    a. the VH FWR1 consists of SEQ ID NO: 15, SEQ ID NO: 19 or SEQ ID NO: 23;
    b. The VH FWR2 consists of SEQ ID NO: 16, SEQ ID NO: 20 or SEQ ID NO:24;
    c. VH FWR3 comprises SEQ ID NO: 17, SEQ ID NO: 21, SEQ ID NO: 25, SEQ ID NO: 43, SEQ ID NO: 44 or SEQ ID NO: 45; and
    d. VH FWR4 consists of SEQ ID NO: 18, SEQ ID NO: 22, or SEQ ID NO: 26;
  iii. the VL region comprises three complementarity determining regions (CDRs) VL CDR1, VL CDR2 and VL CDR3 wherein the VL CDR1 consists of SEQ ID NO: 6, VH CDR2 comprises SEQ ID NO: 7 and VH CDR3 consists of SEQ ID NO: 8;
  iv. the VL region comprises four framework regions (FWR) VL FWR1, VL FWR2, VL FWR3 and VL FWR4 wherein:
    a. the VL FWR1 consists of SEQ ID NO: 27, SEQ ID NO: 31, or SEQ ID NO: 35;
    b. VL FWR2 consists of SEQ ID NO: 28, SEQ ID NO: 32, or SEQ ID NO: 36;
    c. VL FWR3 consists of SEQ ID NO: 29, SEQ ID NO: 33, or SEQ ID NO: 37;
    d. VL FWR4 consists of SEQ ID NO: 30, SEQ ID NO: 34, or SEQ ID NO: 38.

As described above, The FIGURE shows the amino acid sequences of three exemplary humanized VH regions that comprise the VH CDRs of m21G6 (H1-21G6, H2-21G6 and H3-21G6; SEQ ID NOs: 9, 10 and 11, respectively). The FIGURE also shows the amino acid sequences of three exemplary humanized VL regions (L1-21G6, L2-21G6 and L3-21G6; SEQ ID NOs: 12, 13 and 14, respectively). In some embodiments, the antibody or antigen-binding fragments of the invention comprise a VH region that comprises a sequence selected from the group consisting of SEQ ID NO: 9, SEQ ID NO: 10 and SEQ ID NO: 11. In additional aspects, the antibody or antigen-binding fragment has a VL region that comprises a sequence selected from the group consisting of SEQ ID NO: 12, SEQ ID NO: 13 and SEQ ID NO: 14. In yet another embodiment, the antibody or antigen-binding fragment comprises a VH region that comprises a sequence selected from the group consisting of SEQ ID NO: 9, SEQ ID NO: 10 and SEQ ID NO: 11 and comprises a VL region that comprises a sequence selected from the group consisting of SEQ ID NO: 12, SEQ ID NO: 13 and SEQ ID NO: 14.

In some embodiments, the antibody or antigen-binding fragment has a VH region that comprises or consists of SEQ ID NO: 9 and has a VL region that comprises or consists of SEQ ID NO: 12. In other embodiments, the antibody or antigen-binding fragment has a VH region that comprises or consists of SEQ ID NO: 9 and has a VL region that comprises or consists of SEQ ID NO: 13. In another aspect, the antibody or antigen-binding fragment has a VH region that comprises or consists of SEQ ID NO: 9 and the VL region comprises or consists of SEQ ID NO: 14. In a further embodiment, the antibody or antigen-binding fragment has a VH region that comprises or consists of SEQ ID NO: 10 and has a VL region that comprises or consists of SEQ ID NO: 12. In certain additional aspects, the antibody or antigen-binding fragment has a VH region that comprises or consists of SEQ ID NO: 10 and has a VL region that comprises or consists of SEQ ID NO: 13. In an additional embodiment, the antibody or antigen-binding fragment has a VH region that comprises or consists of SEQ ID NO: 10 and has a VL region that comprises or consists of SEQ ID NO: 14. In another aspect of the invention, the antibody or antigen-binding fragment of claim 1 has a VH region that comprises or consists of SEQ ID NO: 11 and a VL region that comprises or consists of SEQ ID NO: 12. In another embodiment, the antibody or antigen-binding fragment has a VH region that comprises or consists of SEQ ID NO: 11 and a VL region that comprises or consists of SEQ ID NO: 13. In another embodiment, the antibody or antigen-binding fragment has a VH region that comprises or consists of SEQ ID NO: 11 and a VL region that comprises or consists of SEQ ID NO: 14.

In certain aspects of the invention, the isotype of the constant region of the antibodies or antigen-binding fragments of the invention is IgG1, IgG2, IgG3, or IgG4. In some embodiments, the isotype of the IgG constant region is IgG1. In other embodiments, the isotype of the IgG constant region is IgG4. In some embodiments, the antibody or antigen-binding fragment thereof have a human IgG1 constant domain or a human IgG4 constant domain. In additional aspects, the antibody or antigen-binding fragment has a human Ig kappa constant domain. The term "isotype" refers to the classification of an antibody's heavy or light chain constant region. The constant domains of antibodies are not involved in binding to antigen, but have various effector functions. Depending on the amino acid sequence of the heavy chain constant region, a human or humanized antibody can be deemed to belong to one of five major classes of immunoglobulins: IgA, IgD, IgE, IgG, and IgM. Many of these classes of immunoglobulins, for example the IgG class, can be divided into subclasses (isotypes), for example, IgG1, IgG2, IgG3, and IgG4. Human light chain constant regions are classified into two major classes, kappa and lambda.

When the positions of amino acid residues are referred to by number herein, it is to be understood that Kabat numbering system is used, unless otherwise indicated. Kabat numbering is described in Kabat et al. (1991) Sequences of Proteins of Immunological Interest, Publication No. 91-3242, National Institutes of Health, National Technical Information Service (hereinafter "Kabat"). Immunoglobulin sequences can be numbered according to Kabat by performing an alignment with the Kabat reference sequence. As such, the Kabat numbering system provides a uniform system for numbering immunoglobulin chains.

The present invention is directed to humanized antibodies wherein the CDRs are from the murine 21G6 antibody and wherein the framework regions are from a human immunoglobulin. It will be understood, that humanized antibodies can comprise amino acid residues that are not found in the recipient antibody or in the donor antibody. For example, such changes in the amino acid sequence can be made to improve binding to the antigen (for example, the N2 peptide) and/or to reduce immunogenicity. Therefore, the present invention encompasses the antibodies or antigen-binding fragments described herein wherein specific amino acids have been substituted, deleted or added. Amino acid substitutions, deletions or additions can be made to the antibodies or antigen-binding fragments thereof to improve or refine the properties of the antibody or fragment, for example amino acid change can be made to inhibit or block inflammation. For example, asparagine at position 297 (Asn 297) of the IgG constant region can be replaced with an alternative amino acid to reduce glycosylation and decrease activation of complement and binding to the Fc receptor. See, for example, Leatherbarrow et al. (1985) Effector functions of a monoclonal aglycosylated mouse IgG2a: binding and activation of complement component C1 and interaction with human monocyte Fc receptor. *Mol Immunol* 22(4):407-415; Tao et al. (1989) Studies of aglycosylated chimeric mouse-human IgG. Role of carbohydrate in the structure and effector functions mediated by the human IgG constant region. *J Immunol* 143(8):2595-2601; Kabat (1987) Sequences of Proteins of Immunological Interest (In: US Department of Human Services), and Sazinsky et al. (2008), Aglycosylated immunoglobulin $G_1$ variants productively engage activating Fc receptors, *PNAS* 105(51): 20167-20172, the contents of each of which are expressly incorporated by reference herein. Glycosylation can be reduced, for example, by replacing the asparagine at position 297 (Asn 297) with an alternative amino acid, for example, alanine, glutamine, histidine or glycine. In some embodiments, Asn 297 can be replaced with glutamine. In certain aspects, the antibody or antigen-binding fragment has a human IgG1 constant domain that is aglycosylated.

In some embodiments, the penultimate amino acid in the third framework of the VH (VH FWR3) of each of H1-21G6, H2-21G6 and H3-21G6 (SEQ ID NOs: 17, 21 and 25, respectively) can be changed from threonine to alanine. The amino acid sequences SEQ ID NOs: 39, 40 and 41 are sequences for the VH FWR3 of each of H1, H2 and H3 wherein the penultimate amino acid (threonine) has been replaced with alanine:

```
H1 VH FWR3 with amino acid mutation to alanine
KATLTVDKSASTAYMELSSLRSEDTAVYYCAR. (SEQ ID NO: 39)

H2 VH FWR3 with amino acid mutation to alanine
KATMTVDKSTSTAYMELRSLRSDDSAVYYCAR. (SEQ ID NO: 40)

H3 VH FWR3 with amino acid mutation to alanine
KATITVDKSTSTAYMELSSLRSEDTAVYYCAR. (SEQ ID NO: 41)
```

The italicized alanine above represents the change from threonine to alanine. The amino acid sequences SEQ ID NOs: 43, 44, and 45 are sequences for the H1, H2 and H3 VH regions wherein the penultimate amino acid (threonine) of the FWR3 is replaced with alanine:

```
H1 VH with amino acid mutation to alanine
in FWR3
                                    (SEQ ID NO: 43)
QVQLVQSGAEVVKPGASVKLSCKASGYTFTSYYMYWVKQAPGQGLEWIGG

INPSNGGTNFNEKFKSKATLTVDKSASTAYMELSSLRSEDTAVYYCARWG

YDREWFAYWGQGTLVTVSS.

H2 VH with amino acid mutation to alanine
in FWR3
                                    (SEQ ID NO: 44)
QVQLVQSGAEVKKPGASVKVSCKASGYTFTSYYMYWVRQAPGQGLEWIGG

INPSNGGTNFNEKFKSKATMTVDKSTSTAYMELRSLRSDDSAVYYCARWG

YDREWFAYWGQGTLVTVSS.

H3 with amino acid mutation to alanine
in FWR3
                                    (SEQ ID NO: 45)
QVQLVQSGAEVKKPGSSVKVSCKASGYTFTSYYMYWVRQAPGQGLEWIGG

INPSNGGTNFNEKFKSKATITVDKSTSTAYMELSSLRSEDTAVYYCARWG

YDREWFAYWGQGTLVTVSS.
```

The italicized alanine above represents the change from threonine to alanine.

Amino acid modifications that may increase stability and/or increase affinity are also contemplated herein. Additional specific amino acid variants contemplated by the invention are variants of H2-21G6 VH and a variant of the murine 21G6 VL kappa chain:

```
Amino Acid Variant of H2 VH
                                    (SEQ ID NO: 42)
QVQLVQSGAELVKKPGASLKVSCKASGYTFTSYYMYWVRQAPGQGLEWIG

GINPSNGGTNFNEKFKGRVTITRDKSTSTAYMELRSLRSEDSAVYYCARW

GYDREWFAYWGQGTLVTVSS.
```

Amino Acid Variant of kappa chain (m21G6 VL)
(SEQ ID NO: 46)
EIVLTQSPGTLSLSP GERATLSCRAS KSLLHSNGNTYLYWYQQKPGQA

PRLLIYRMSNRATGIPA RFSGSGSGTDFTLTISSLEPEDFAVYYC

MQHLEYPFTFGQGTKLEIKR.

Additional amino acid modifications include amino acid variants of the H2 VH amino acid sequence (SEQ ID NO: 42), wherein the amino acid at position 65 is replaced with glycine, the amino acid at position 66 is replaced with arginine, the amino acid at position 67 is replaced with valine or phenylalanine, the amino acid at position 69 is replaced with isoleucine, the amino acid at position 71 is replaced with arginine and/or the amino acid at position 85 can be replaced with glutamic acid.

The invention also encompasses an antibody or antigen-binding fragment thereof wherein an alanine at position 78 (Ala 78) of the VH is replaced with phenylalanine.

In certain embodiments, the antibody or antigen-binding fragment has a human IgG4 constant domain wherein serine at position 228 (Ser 228) is replaced with proline.

Additional modifications can also be made within the Fc region, typically to alter one or more functional properties of the antibody, such as serum half-life, complement fixation, Fc receptor binding, protein stability and/or antigen-dependent cellular cytotoxicity, or lack thereof. In addition, an antibody of the invention can be chemically modified (e.g., one or more chemical moieties can be attached to the antibody). For example, the class of an antibody can be "switched" by known techniques. Such techniques include, e.g., the use of direct recombinant techniques (see e.g., U.S. Pat. No. 4,816, 397) and cell-cell fusion techniques (see e.g., U.S. Pat. No. 5,916,771). For example, an antibody that was originally produced as an IgM molecule may be class switched to an IgG antibody. Class switching techniques also may be used to convert one IgG subclass to another, e.g., from IgG1 to IgG2. Thus, the effector function of the antibodies of the invention may be changed by isotype switching to, e.g., an IgG1, IgG2, IgG3, IgG4, IgD, IgA, IgE, or IgM antibody for various therapeutic uses. Exemplary cDNA sequences for constant regions are available from GenBank, for example, each of which incorporated by reference in its entirety, are as follows: Human IgG1 constant heavy chain region: GenBank Accession No.: J00228; Human IgG2 constant heavy chain region: GenBank Accession No.: J00230; Human IgG3 constant heavy chain region: GenBank Accession No.: X04646; Human IgG4 constant heavy chain region: GenBank Accession No.: K01316; and Human kappa light chain constant region: GenBank Accession No.: J00241. The hinge region of CH$_1$ can also be modified such that the number of cysteine residues in the hinge region is increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. The Fc hinge region of an antibody can also be mutated to decrease the biological half-life of the antibody. In another embodiment, the antibody is modified to increase its biological half-life. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both to Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 and 239 are altered to thereby alter the ability of the antibody to fix complement. This approach is described further in PCT Publication WO 94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) J. Biol. Chem. 276:6591-6604).

An antibody or antigen-binding fragment described herein can be chemically modified based on linkage to a polymer. The polymer is typically water soluble so that the antibody to which it is attached does not precipitate in an aqueous environment, such as a physiological environment. The polymer can have a single reactive group, such as an active ester for acylation or an aldehyde for alkylation, so that the degree of polymerization may be controlled. An exemplary reactive aldehyde is polyethylene glycol propionaldehyde, which is water stable, or mono $C_1$-$C_{10}$ alkoxy or aryloxy derivatives thereof (see U.S. Pat. No. 5,252,714). The polymer can be branched or unbranched. For therapeutic use of the end-product preparation, the polymer is pharmaceutically acceptable. The water soluble polymer, or mixture thereof if desired, can be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

An antibody fragment or antigen-binding fragment is a derivative of an antibody that is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv, diabody, minibody, Fc, Fd fragments, and single chain antibodies.

Antibody fragments can be produced by methods known in the art. For example, the antibody fragment can be enzymatically or chemically produced by fragmentation of an intact antibody, or the fragment can be produced recombinantly. The antibody fragment can optionally be a single chain antibody fragment. Alternatively, the fragment can comprise multiple chains which are linked together, for instance, by disulfide linkages. In addition, digestion of an antibody with pepsin yields F(ab')$_2$ fragments and multiple small fragments. Mercaptoethanol reduction of an antibody yields individual heavy and light chains. Digestion of an antibody with papain yields individual Fab fragments and the Fc fragment. The fragment can also optionally be a multimolecular complex. A functional antibody fragment can for example comprise at least about 50 amino acids. In some embodiments, the functional antibody fragment can comprise at least about 200 amino acids.

Humanized antibodies and antigen-binding fragment thereof described herein can be produced using techniques known in the art, including, but not limited to, CDR-grafting (see, for example, European Patent No. EP 239,400; WO 91/09967; and U.S. Pat. Nos. 5,225,539, 5,530,101, and 5,585,089, the contents of each of which incorporated by reference), veneering or resurfacing (see, for example, European Patent Nos. EP 592,106 and EP 519,596; Padlan, 1991, Molecular Immunology 28(4/5):489-498; Studnicka et al., 1994, Protein Engineering, 7(6):805-814; and Roguska et al., 1994, Proc. Natl. Acad. Sci., 91:969-973, each of which is incorporated herein by its entirety by reference), chain shuffling (see, e.g., U.S. Pat. No. 5,565,332, which is incorporated herein in its entirety by reference), and techniques disclosed in, for example, U.S. Pat. No. 6,407,213, U.S. Pat. No. 5,766, 886, PCT Publication No. WO 9317105, Tan et al., J. Immunol., 169:1119-25 (2002), Caldas et al., Protein Eng., 13(5): 353-60 (2000), Morea et al., Methods, 20(3):267-79 (2000), Baca et al., J. Biol. Chem., 272(16):10678-84 (1997), Roguska et al, Protein Eng., 9(10):895-904 (1996), Couto et al., Cancer Res., 55 (23 Supp): 5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated by reference herein.

The humanized antibody can be produced by, for example, by constructing cDNAs encoding the humanized variable regions, inserting each of them into an expression vector for animal cells comprising genes encoding the heavy chain and light chain of a human antibody to thereby construct a vector for expression of humanized antibody, and introducing it into an animal cell to express and produce the humanized antibody. The invention encompasses a nucleotide sequence that encodes an antibody or antigen-binding fragment described herein. Also encompassed is an expression vector comprising a nucleotide sequence that encodes an antibody or antigen-binding fragment of the invention and an isolated cell comprising said vector. The antibody or antigen-binding fragment can be produced, for example, by culturing a cell comprising said expression vector, recovering the antibody or fragment thereof from the cultured cells or culture medium. "Cells" or "host cells" are terms used interchangeably herein. It is understood that such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

As described above, the antibody and antigen-binding fragment of the invention bind the N2 epitope and can therefore be used for treating a number of inflammatory diseases and conditions that are triggered by binding of natural IgM antibodies. For instance, the antibodies or fragments thereof can be used to treat inflammatory diseases or conditions such as reperfusion injury, ischemia injury, stroke, autoimmune hemolytic anemia, idiopathic thrombocytopenic purpura, rheumatoid arthritis, celiac disease, hyper-IgG immunodeficiency, arteriosclerosis, coronary artery disease, sepsis, myocarditis, encephalitis, transplant rejection, hepatitis, thyroiditis (e.g., Hashimoto's thyroiditis, Graves disease), osteoporosis, polymyositis, dermatomyositis, drug- or chemotherapy-induced inflammation (e.g., drug or chemotherapy induced nephritis, endocarditis, nephritis), Type I diabetes, gout, dermatitis, alopecia areata, systemic lupus erythematosus, lichen sclerosis, ulcerative colitis, diabetic retinopathy, pelvic inflammatory disease, periodontal disease, arthritis, juvenile chronic arthritis (e.g., chronic iridocyclitis), psoriasis, osteoporosis, nephropathy in diabetes mellitus, asthma, pelvic inflammatory disease, chronic inflammatory liver disease, chronic inflammatory lung disease, lung fibrosis, liver fibrosis, rheumatoid arthritis, chronic inflammatory liver disease, chronic inflammatory lung disease, lung fibrosis, liver fibrosis, Crohn's disease, ulcerative colitis, burn injury (or thermal injury), and other acute and chronic inflammatory diseases of the Central Nervous System (CNS; e.g., multiple sclerosis), gastrointestinal system, the skin and associated structures, the immune system, the hepato-biliary system, or any site in the body where pathology can occur with an inflammatory component.

The invention encompasses methods of inhibiting the activation of an immune response to the N2 antigen in a subject by administering to a subject an antibody described herein. In a further aspect, the invention encompasses methods of treating an inflammatory disease or condition, for example, ischemia-reperfusion injury, in a subject comprising administering to the subject a pharmaceutical composition comprising an antibody or fragment of the invention.

An inflammatory condition such as reperfusion or ischemic injury can result following a naturally occurring episode, including, for example, a stroke or myocardial infarction. Reperfusion or ischemic injury can also occur during and/or following a surgical procedure. Exemplary surgical procedures that cause can cause injury include a vessel-corrective technique selected from the group consisting of angioplasty, stenting procedure, atherectomy, and bypass surgery. In an exemplary embodiment, reperfusion or ischemic injury occurs in a cardiovascular tissue, such as the heart.

Data obtained from animal studies can be used in formulating a range of dosage for use in humans. The dosage of an antibody is within a range of circulating concentrations that include the $ED_{50}$ with little or no toxicity. The dosage can vary within this range depending upon the dosage form employed and the route of administration. For an antibody or fragment thereof used in the method described herein, the therapeutically effective dose can be estimated initially from in vitro assays. A dose can be formulated in animal models to achieve a circulating plasma concentration range that includes the $IC_{50}$ (i.e., the concentration of the test compound which achieves a half-maximal inhibition of symptoms) as determined in in vitro assay. This information can be used to more accurately determine useful doses in humans. Levels in plasma may be measured, for example, using enzyme linked immunosorbent assay (ELISA).

In some embodiments, an antibody or fragment thereof can be administered prior to, contemporaneously with, or subsequent to a tissue injury. In some embodiments, the pharmaceutical composition can be administered a few hours, a few days or a few weeks after tissue injury. In some embodiments, an antibody or fragment thereof can be administered prior to tissue injury, for example, in subjects at risk for reperfusion injury such as those patients that are about to undergo surgery. In additional embodiments, the antibody or fragment thereof can be administered.

A "therapeutically effective amount" or an "effective amount" is an amount which, alone or in combination with one or more other active agents, can control, decrease, inhibit, ameliorate, prevent or otherwise affect and/or achieve a recited effect. An effective amount of the agent to be administered can be determined using methods well-known in the art. One of skill in the art would take into account the mode of administration, the disease or condition (if any) being treated and the characteristics of the subject, such as general health, other diseases, age, sex, genotype, body weight and tolerance to drugs. A "patient" can refer to a human subject in need of treatment.

The antibody or fragment of the present invention can be provided in pharmaceutically acceptable carriers or formulated for a variety of modes of administration, including systemic and topical or localized administration. Techniques and formulations generally may be found in Remmington's Pharmaceutical Sciences, Meade Publishing Co., Easton, Pa. In certain embodiments, the antibody or fragment thereof is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, compositions of the invention are formulated into ointments, salves, gels, or creams as generally known in the art.

The pharmaceutical compositions according to the invention are prepared by bringing an antibody or fragment thereof into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include, for example, antimicrobial, anti-oxidants, chelating agents and inert gases. Other pharmaceutically acceptable carriers include aqueous solutions, non-toxic excipients, including salts, preservatives, buffers and the like, as described, for instance, in The Science and Practice of Pharmacy, 20th Edition (Philadelphia College of Pharmacy and Science, 2000) and Remington: The Science and Practice of Pharmacy, 22nd Edition (Pharmaceutical Press and Philadelphia College of Pharmacy at University of the Sciences, 2012), and Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of each of which are hereby incorporated by reference. The pH and exact concentration of the various components of the pharmaceutical composition are adjusted according to routine skills in the art. See Goodman and Gilman's *The Pharmacological Basis for Therapeutics* (7th ed.) and Goodman and Gilman's *The Pharmacological Basis for Therapeutics,* 12th edition, (McGraw Hill Professional Publishing, 2010).

The pharmaceutical compositions can be prepared and administered in dose units. Solid dose units are tablets, capsules and suppositories and including, for example, alginate based pH dependent release gel caps. For treatment of a subject, depending on activity of the pharmaceutical composition, the manner of administration, nature and severity of the disorder, age and body weight of the subject, different daily doses are necessary. Under certain circumstances, however, higher or lower daily doses can be appropriate. The administration of the daily dose can be carried out both by single administration in the form of an individual dose unit or by several smaller dose units and also by multiple administrations of subdivided doses at specific intervals.

The pharmaceutical compositions according to the invention can be administered locally or systemically in a therapeutically effective dose. Amounts effective for this use will, of course, depend on the severity of the disease and the weight and general state of the subject. As discussed above, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Goodman and Gilman's *The Pharmacological Basis for Therapeutics,* 12th edition, (McGraw Hill Professional Publishing, 2010); each of which is herein incorporated by reference.

In one embodiment, the invention provides a pharmaceutical composition useful for administering an antibody or antigen-binding fragment thereof to a subject in need of such treatment. "Administering" the pharmaceutical composition of the invention may be accomplished by any means known to the skilled artisan. A "subject" refers to a mammal, most preferably a human.

The antibody or fragment thereof can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water. Where the disease or disorder is a gastrointestinal disorder oral formulations or suppository formulations are preferred.

Sterile injectable solutions can be prepared by incorporating an antibody or antigen-binding fragment thereof in the required amount (e.g., about 10 µg to about 10 mg/kg) in an appropriate solvent and then sterilizing, such as by sterile filtration. Further, powders can be prepared by standard techniques such as freeze drying or vacuum drying.

In another embodiment, antibody or fragment thereof is prepared with a biodegradable carrier for sustained release characteristics for either sustained release in the GI tract or for target organ implantation with long term active agent release characteristics to the intended site of activity. Biodegradable polymers include, for example, ethylene vinyl acetate, polyanhydrides, polyglycolic acids, polylactic acids, collagen, polyorthoesters, and poly acetic acid. Liposomal formulation can also be used.

Any route of administration compatible with the active principle can be used. In some embodiments, the route of administration is parenteral administration, such as subcutaneous, intramuscular or intravenous injection. The dose of the antibody or antigen-binding fragment thereof to be administered depends on the basis of the medical prescriptions according to age, weight and the individual response of the patient.

The daily non-weighted dosage for the patient can be between about 2.5-5.0 mg/Kg, e.g., about 2.5-3.0 mg/Kg, about 3.0-3.5 mg/Kg, about 3.5-4.0 mg/Kg, about 4.0-4.5 mg/Kg, and about 4.5-5.0 mg/Kg.

The pharmaceutical composition for parenteral administration can be prepared in an injectable form comprising the active principle and a suitable vehicle. Vehicles for the parenteral administration are well known in the art and comprise, for example, water, saline solution, Ringer solution and/or dextrose. The vehicle can contain small amounts of excipients in order to maintain the stability and isotonicity of the pharmaceutical preparation. The preparation of the cited solutions can be carried out according to the ordinary modalities.

The present invention has been described with reference to the specific embodiments, but the content of the description comprises all modifications and substitutions, including conservative amino acid substitutions, which can be brought by a person skilled in the art without extending beyond the meaning and purpose of the claims. The compositions can, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least about 30%, preferably at least about 40%, more preferably at least about 50%, about 60%, and even more preferably at least about 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences and the percent homology between two sequences is a function of the number of conserved positions shared by the sequences, taking into account the number of gaps, and the length of each gap, which need to be introduced for optimal alignment of the two sequences. The comparison of sequences and determination of percent identity and/or homology between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GAP program in the GCG software package (available on the internet at the Accelrys website, more specifically at http://www.accelrys.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available on the world wide web with the extension gcg.com), using a NWSgapdna CMP matrix and a gap weight of 40, 50, 60, 70; or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frame shift gap penalty of 5.

The percent identity and/or homology between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Stringency hybridization" or "hybridizes under low stringency, medium stringency, high stringency, or very high stringency conditions" is used herein to describe conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. Calculations of homology or sequence identity between sequences (the terms are used interchangeably herein) are performed as described above.

The amino acid sequences referred to in the present application are listed below with the corresponding sequence identifier (SEQ ID NO):

m21G6 VH (SEQ ID NO: 1)
QVQLQQPGAELVKPGASVKLSCKASGYTFT<u>SYYMY</u>WVKQRPGQGLEWIG<u>G</u>

<u>INPSNGGTNFNEKFKS</u>KATLTVDKSSSTAYMQLSSLTSEDSAVYYCTRW<u>G</u>

<u>YDREWFAY</u>WGQGTLVTVSA.

m21G6 VL (SEQ ID NO: 2)
DIVMTQAAPSVPVTPGESVSISCRSSKSLLHSNGNTYLYWFLQRPGQSPQ
VLIYRMSNLASGVPDRFSGSGSGTAFTLRISRVEAEDVGVYYCMQHLEYP
FTFGSGTKLEIKR.

VH CDR1

(SEQ ID NO: 3)
SYYMY.

VH CDR2

(SEQ ID NO: 4)
GINPSNGGTNFNEKFKS.

VH CDR3

(SEQ ID NO: 5)
GYDREWFAY.

VL CDR1

(SEQ ID NO: 6)
RSSKSLLHSNGNTYLY.

VL CDR2

(SEQ ID NO: 7)
RMSNLAS.

VL CDR3

(SEQ ID NO: 8)
MQHLEYPFT.

H1-21G6 Vh (SEQ ID NO: 9)
QVQLVQSGAEVVKPGASVKLSCKASGYTFTSYYMYWVKQAPGQGLEWIGG
INPSNGGTNFNEKFKSKATLTVDKSASTAYMELSSLRSEDTAVYYCTRWG
YDREWFAYWGQGTLVTVSS.

H2-21G6 Vh (SEQ ID NO: 10)
QVQLVQSGAEVKKPGASVKVSCKASGYTFTSYYMYWVRQAPGQGLEWIGG
INPSNGGTNFNEKFKSKATMTVDKSTSTAYMELRSLRSDDSAVYYCTRWG
YDREWFAYWGQGTLVTVSS.

H3-21G6 Vh (SEQ ID NO: 11)
QVQLVQSGAEVKKPGSSVKVSCKASGYTFTSYYMYWVRQAPGQGLEWIGG
INPSNGGTNFNEKFKSKATITVDKSTSTAYMELSSLRSEDTAVYYCTRWG
YDREWFAYWGQGTLVTVSS.

L1-21G6 Vl (PopVk, CLL)

(SEQ ID NO: 12)
DIVMTQSPATLSVSPGERATISCRSSKSLLHSNGNTYLYWFQQKPGQPPK
VLIYRMSNLASGVPARFSGSGSGTDFTLTISSVEPEDFATYYCMQHLEYP
FTFGGGTKLEIKR.

L2-21G6 Vl (SEQ ID NO: 13)
DIVMTQSPLSLPVTPGEPASISCRSSKSLLHSNGNTYLYWFLQKPGQSPQ
LLIYRMSNLASGVPDRFSGSGSGTDFTLKISRVEAEDVGVYYCMQHLEYP
FTFGQGTKLEIKR.

L3-m21G6 Vl (SEQ ID NO: 14)
DIVMTQTPLSLSYTPGQPASISCRSSKSLLHSNGNTYLYWFLQKPGQSPQ
LLIYRMSNLASGVPDRFSGSGSGTDFTLKISRVEAEDVGVYYCMQHLEYP
FTFGQGTKLEIKR.

H1 VH FWR1

(SEQ ID NO: 15)
QVQLVQSGAEVVKPGASVKLSCKASGYTFT.

H1 VH FWR2

(SEQ ID NO: 16)
WVKQAPGQGLEWIG.

H1 VH FWR3

(SEQ ID NO: 17)
KATLTVDKSASTAYMELSSLRSEDTAVYYCTR.

H1 VH FWR4

(SEQ ID NO: 18)
WGQGTLVTVSS.

H2 VH FWR1

(SEQ ID NO: 19)
QVQLVQSGAEVKKPGASVKVSCKASGYTFT.

H2 VH FWR2

(SEQ ID NO: 20)
WVRQAPGQGLEWIG.

H2 VH FWR3

(SEQ ID NO: 21)
KATMTVDKSTSTAYMELRSLRSDDSAVYYCTR.

H2 VH FWR4

(SEQ ID NO: 22)
WGQGTLVTVSS.

H3 VH FWR1

(SEQ ID NO: 23)
QVQLVQSGAEVKKPGSSVKVSCKASGYTFT.

H3 VH FWR2

(SEQ ID NO: 24)
WVRQAPGQGLEWIG.

H3 VH FWR3

(SEQ ID NO: 25)
KATITVDKSTSTAYMELSSLRSEDTAVYYCTR.

H3 VH FWR4

(SEQ ID NO: 26)
WGQGTLVTVSS.

L1 VL FWR1

(SEQ ID NO: 27)
DIVMTQSPATLSVSPGERATISC.

L1 VL FWR2

(SEQ ID NO: 28)
WFQQKPGQPPKVLIY.

L1 VL FWR3

(SEQ ID NO: 29)
GVPARFSGSGSGTDFTLTISSVEPEDFATYYC.

L1 VL FWR4

(SEQ ID NO: 30)
FGGGTKLEIKR.

L2 VL FWR1

(SEQ ID NO: 31)
DIVMTQSPLSLPVTPGEPASISC.

L2 VL FWR2

(SEQ ID NO: 32)
WFLQKPGQSPQLLIY.

L2 VL FWR3

(SEQ ID NO: 33)
GVPDRFSGSGSGTDFTLKISRVEAEDVGVYYC.

L2 VL FWR4

(SEQ ID NO: 34)
FGQGTKLEIKR.

-continued

L3 VL FWR1
(SEQ ID NO: 35)
DIVMTQTPLSLSYTPGQPASISC.

L3 VL FWR2
(SEQ ID NO: 36)
WFLQKPGQSPQLLIY.

L3 VL FWR3
(SEQ ID NO: 37)
GVPDRFSGSGSGTDFTLKISRVEAEDVGVYYC.

L3 VL FWR4
(SEQ ID NO: 38)
FGQGTKLEIKR.

H1 VH FWR3 with amino acid mutation to alanine
(SEQ ID NO: 39)
KATLTVDKSASTAYMELSSLRSEDTAVYYCAR.

H2 VH FWR3 with amino acid mutation to alanine
(SEQ ID NO: 40)
KATMTVDKSTSTAYMELRSLRSDDSAVYYCAR.

H3 VH FWR3 with amino acid mutation to alanine
(SEQ ID NO: 41)
KATITVDKSTSTAYMELSSLRSEDTAVYYCAR.

Amino Acid Variant of H2 Vh
(SEQ ID NO: 42)
QVQLVQSGAEVKKPGASLKVSCKASGYTFTSYYMYWVRQAPGQGLEWIGG

INPSNGGTNFNEKFKGRVTITRDKSTSTAYMELRSLRSEDSAVYYCARWG

YDREWFAYWGQGTLVTVSS.

H1 VH with amino acid mutation to alanine
in FWR3
(SEQ ID NO: 43)
QVQLVQSGAEVVKPGASVKLSCKASGYTFTSYYMYWVKQAPGQGLEWIGG

INPSNGGTNFNEKFKSKATLTVDKSASTAYMELSSLRSEDTAVYYCARWG

YDREWFAYWGQGTLVTVSS.

H2 VH with amino acid mutation to alanine
in FWR3
(SEQ ID NO: 44)
QVQLVQSGAEVKKPGASVKVSCKASGYTFTSYYMYWVRQAPGQGLEWIGG

INPSNGGTNFNEKFKSKATMTVDKSTSTAYMELRSLRSDDSAVYYCARWG

YDREWFAYWGQGTLVTVSS.

H3 with amino acid mutation to alanine
in FWR3
(SEQ ID NO: 45)
QVQLVQSGAEVKKPGSSVKVSCKASGYTFTSYYMYWVRQAPGQGLEWIGG

INPSNGGTNFNEKFKSKATITVDKSTSTAYMELSSLRSEDTAVYYCARWG

YDREWFAYWGQGTLVTVSS.

Amino Acid Variant of kappa chain (m21G6 V1)
(SEQ ID NO: 46)
EIVLTQSPGTLSLSP GERATLSCRAS KSLLHSNGNTYLYWYQQKPGQA

PRLLIYRMSNRATGIPA RFSGSGSGTDFTLTISSLEPEDFAVYYC

MQHLEYPFTFGQGTKLEIKR.

N2 peptide
(SEQ ID NO: 47)
LMKNMDPLNDNV.

Peptide sequence
(SEQ ID NO: 48)
LMKNMDPLNDNI.

The invention is illustrated by the following non-limiting example.

EXEMPLIFICATION

Example 1

Humanization of Murine Antibody 21G6

Murine 21G6 is an IgG1 heavy chain and kappa light chain that was raised against the non-muscle myosin neo-epitope N2 12 mer sequence: LMKNMDPLNDNV (SEQ ID NO: 47). The murine 21G6 antibody is described in more detail in U.S. Pat. No. 8,324,352, the contents of which are expressly incorporated herein. Using the IMGT database (http://www.imgt.org), a search was performed to identify the human germline antibody sequences with the greatest homology to the murine 21G6 antibody. In addition, a BLAST search was performed to identify homologous human non-germline antibodies. The sequences shown in The FIGURE were determined to have the highest amino acid homology.

The FIGURE shows a sequence comparison for the murine 21G6 heavy chain variable (VH) region variable heavy and the humanized heavy chain variable regions (VH) H1-21G6, H2-21G6 and H3-21G6 and also shows a sequence comparison of the murine 21G6 light chain variable (VL) region and the humanized light chain variable regions light chain (VL) regions L1-21G6, L2-21G6 and L3-21G6.

The H1-21G6 and L1-21G6 frameworks were derived from B-cells obtained from lupus and chronic lymphocytic leukemia (CLL) patients for the heavy and light chains, respectively. The remaining sequences represent the germline sequences with the highest homology that encode productive antibody. All of the humanized sequences maintain the murine 21G6 CDR regions which are shown inside the boxes in The FIGURE. The humanized variable regions were cloned into a vector containing wild type human IgG1, human IgG1 containing a mutation at amino acid 297 (Asn 297 to Q297), human IgG4 containing a mutation at amino acid 228 (serine to proline) and human kappa light chain. Each antibody (heavy and light) combination was expressed by transient co-transfection in 293A cells (in the presence of low Ig serum). The antibody containing supernatants were collected and analyzed for binding to the N2 peptide by ELISA and Biacore. All experiments were performed using a Biacore X100 system. For antibody capture experiments, a CM5 chip was prepared by 10 ul/minute injection of EDC/NHS (N-ethyl-N'-(3-dimethylaminopropyl)carbodiimide (EDC), N-hydroxysuccinimide (NHS) for 7 minutes, followed by a 10 ul/minute injection of anti-human Fc (GE Lifesciences) at a concentration of 25 ug/ml in sodium acetate at pH 5 for 3 minutes. Ethanolamine-HCl was injected for 7 minutes at 10 ul/minute. The chimeric or humanized antibodies were captured onto flow cell 2 and N2 peptide at varying concentrations was flowed over flow cells 1 and 2 at a rate of 30 ul/minute with a contact time of 120 seconds and a dissociation period of 120 seconds. Complete removal of captured antibody was accomplished by regeneration with 3M MgCl2 for 30 seconds at a flow rate of 10 ul/minute. For peptide immobilized experiments, a CM5 chip was prepared by 10 ul/minute injection of EDC/NHS (N-ethyl-N'-(3-dimethylaminopropyl)carbodiimide (EDC), N-hydroxysuccinimide (NHS) for 7 minutes, followed by a 10 ul/minute injection of Neutravidin (ThermoFisher Pierce) at a concentration of 5 ug/ml in sodium acetate, pH 5 to an immobilization response of 100-200RU. Ethanolamine-HCl was injected for 7 minutes at 10 ul/minute. Biotin-labeled N2 peptide was captured on flow channel 2 with the goal of an experimental Rmax of about 50-100RU. Purified chimeric or humanized antibodies were flowed over both flow channels at a rate of 30 ul/min for a contact time of 120 seconds and allowed to dissociate for 600 seconds. Regeneration was achieved with glycine pH 1.7 for 30 seconds thus retaining an active surface. The apparent affinity constants and antibody on/off rates are shown in Tables 1A, 1B and 2 below:

TABLE 1A

Apparent Affinity Constants for variable regions and wild type human IgG1 heavy chain (Immobilized Antibody, N2 peptide in solution)

| Heavy Chain | Light Chain | Kd (uM) by IgG capture |
|---|---|---|
| H1 | L2 | 17 |
| H1 | L3 | 20.9 |
| H1 | L1 | 6.6-7.7 |
| H2 | L2 | 6.4-8.4 |
| H2 | L3 | 9.56 |
| H2 | L1 | 9.8-11 |
| H3 | L2 | 11.5 |
| H3 | L3 | 9.38 |
| H3 | L1 | 7.9 |
| m21G6 | m21G6 | 4-6 |
| CHIgG1 (human heavy chain constant region IgG1) | Ch | 6-7 |
| CHIgG4 (human heavy chain constant region IgG4) | Ch | 4.1 |

TABLE 1B

Apparent Affinity Constants for variable regions and human IgG1 heavy chain with mutation at position 297 from Asn to Gln (Immobilized Antibody, N2 peptide in solution)

| Heavy Chain (N297Q) | Light Chain | Kd (uM) by IgG capture |
|---|---|---|
| H1 | L2 | TBD |
| H1 | L3 | TBD |
| H1 | L1 | 9 |
| H2 | L2 | 3.1-3.7 |
| H2 | L3 | 8.8 |
| H2 | L1 | TBD |
| H3 | L2 | TBD |
| H3 | L1 | 20 |
| H3 | L3 | TBD |
| CHIgG1 (human heavy chain constant region IgG1) | CH | 5.6 |

(TBD indicated "to be determined")

TABLE 2

Antibody on- and off-rates (immobilized N2, antibody in solution)

| Heavy Chain | Light Chain | Ka (e+4) (on-rate) | kd (e−3) (off-rate) | Affinity (nM) kd/ka (monovalent) | Steady state affinity (nM) |
|---|---|---|---|---|---|
| H1 | L3 | 0.63 | 9.93 | 1580 | 1000 |
| H1 | L1 | 1.5-4.3 | 4.3-6.5 | 100-430 | 320 |
| H2 | L2 | 2.0-3.2 | 8.6-9.1 | 280-420 | 240 |
| H2 | L3 | 2.4 | 3.5 | 140 | 680 |
| H2 | L1 | 0.7 | 4.63 | 660 | NA |
| H3 | L2 | 1.2 | 7.2 | 640 | NA |
| H3 | L3 | 0.60 | 5.61 | 900 | NA |
| H3 | L1 | 2.0-5.2 | 3-6.5 | 300 | 280 |
| ch21G6 N297Q (human heavy chain constant region IgG1 with Q297 mutation) | ch21G6 | 7-10 | 7-19 | 100-200 | 196-240 |
| ch21G6 IgG4 (human heavy chain constant region IgG4) | ch21G6 | 5 | 40 | 800 | 113 |
| m21G6 | m21G6 | 1-11 | 5-53 | 200-400 | 313-540 |

As determined by t-test, there was no significant difference between murine 21G6 and H1/L1 and murine 21G6 and H2/L2. (Murine 21G6: n=4; 9r/9r: n=3; 69/9r: n=2).

While this invention has been particularly shown and described with references to preferred embodiments thereof, it will be understood by those skilled in the art that various changes in form and details may be made therein without departing from the scope of the invention encompassed by the appended claims.

What is claimed is:

1. A humanized anti-N2 antibody or antigen-binding fragment thereof comprising a heavy chain variable (VH) region and a light chain variable (VL) region, wherein:
   i. the VH region comprises three complementarity determining regions (CDRs) VH CDR1, VH CDR2 and VH CDR3 wherein the VH CDR1 comprises SEQ ID NO: 3, VH CDR2 comprises SEQ ID NO: 4 and VH CDR3 comprises SEQ ID NO: 5;
   ii. the VH region comprises four framework regions (FWR) VH FWR1, VH FWR2, VH FWR3 and VH FWR4 wherein:
      a. the VH FWR1 comprises SEQ ID NO: 15, SEQ ID NO: 19 or SEQ ID NO: 23;
      b. the VH FWR2 comprises SEQ ID NO: 16, SEQ ID NO: 20 or SEQ ID NO:24;
      c. VH FWR3 comprises SEQ ID NO: 17, SEQ ID NO: 21, SEQ ID NO: 25, SEQ ID NO: 43, SEQ ID NO: 44 or SEQ ID NO: 45; and
      d. VH FWR4 comprises SEQ ID NO: 18, SEQ ID NO: 22, or SEQ ID NO: 26;
   iii. the VL region comprises three complementarity determining regions (CDRs) VL CDR1, VL CDR2 and VL CDR3 wherein the VL CDR1 comprises SEQ ID NO: 6, VH CDR2 comprises SEQ ID NO: 7 and VH CDR3 comprises SEQ ID NO: 8;
   iv. the VL region comprises four framework regions (FWR) VL FWR1, VL FWR2, VL FWR3 and VL FWR4 wherein:
      a. the VL FWR1 comprises SEQ ID NO: 27, SEQ ID NO: 31, or SEQ ID NO: 35;
      b. VL FWR2 comprises SEQ ID NO: 28, SEQ ID NO: 32, or SEQ ID NO: 36;
      c. VL FWR3 comprises SEQ ID NO: 29, SEQ ID NO: 33, or SEQ ID NO: 37; and
      d. VL FWR4 comprises SEQ ID NO: 30, SEQ ID NO: 34, or SEQ ID NO: 38.

2. The antibody or antigen-binding fragment of claim 1, wherein:
   i. the VH region comprises three complementarity determining regions (CDRs) VH CDR1, VH CDR2 and VH CDR3 wherein the VH CDR1 consists of SEQ ID NO:3, VH CDR2 consists of SEQ ID NO: 4 and VH CDR3 consists of SEQ ID NO: 5;
   ii. the VH region comprises four framework regions (FWR) VH FWR1, VH FWR2, VH FWR3 and VH FWR4 wherein:
      a. the VH FWR1 consists of SEQ ID NO: 15, SEQ ID NO: 19 or SEQ ID NO: 23;
      b. The VH FWR2 consists of SEQ ID NO: 16, SEQ ID NO: 20 or SEQ ID NO:24;
      c. VH FWR3 comprises SEQ ID NO: 17, SEQ ID NO: 21, SEQ ID NO: 25, SEQ ID NO: 43, SEQ ID NO: 44 or SEQ ID NO: 45; and
      d. VH FWR4 consists of SEQ ID NO: 18, SEQ ID NO: 22, or SEQ ID NO: 26;
   iii. the VL region comprises three complementarity determining regions (CDRs) VL CDR1, VL CDR2 and VL CDR3 wherein the VL CDR1 consists of SEQ ID NO: 6, VH CDR2 comprises SEQ ID NO: 7 and VH CDR3 consists of SEQ ID NO: 8;
   iv. the VL region comprises four framework regions (FWR) VL FWR1, VL FWR2, VL FWR3 and VL FWR4 wherein:
      a. the VL FWR1 consists of SEQ ID NO: 27, SEQ ID NO: 31, or SEQ ID NO: 35;
      b. VL FWR2 consists of SEQ ID NO: 28, SEQ ID NO: 32, or SEQ ID NO: 36;
      c. VL FWR3 consists of SEQ ID NO: 29, SEQ ID NO: 33, or SEQ ID NO: 37; and
      d. VL FWR4 consists of SEQ ID NO: 30, SEQ ID NO: 34, or SEQ ID NO: 38.

3. The antibody or antigen-binding fragment of claim 1, wherein the VH region comprises a sequence selected from the group consisting of SEQ ID NO: 9, SEQ ID NO: 10 and SEQ ID NO: 11.

4. The antibody or antigen-binding fragment of claim 1, wherein the VL region comprises a sequence selected from the group consisting of SEQ ID NO: 12, SEQ ID NO: 13 and SEQ ID NO: 14.

5. The antibody or antigen-binding fragment of claim 1, wherein the VH region consists of a sequence selected from the group consisting of SEQ ID NO: 9, SEQ ID NO: 10 and SEQ ID NO: 11.

6. The antibody or antigen-binding fragment of claim 1, wherein the VL region consists of a sequence selected from the group consisting of SEQ ID NO: 12, SEQ ID NO:13 and SEQ ID NO: 14.

7. The antibody or antigen-binding fragment of claim 1, wherein the VH region consists of the amino acid sequence of SEQ ID NO: 9 and the VL region consists of the amino acid sequence of SEQ ID NO: 12.

8. The antibody or antigen-binding fragment of claim 1, wherein the VH region consists of the amino acid sequence of SEQ ID NO: 9 and the VL region consists of the amino acid sequence of SEQ ID NO: 13.

9. The antibody or antigen-binding fragment of claim 1, wherein the VH region consists of the amino acid sequence of SEQ ID NO: 9 and the VL region consists of the amino acid sequence of SEQ ID NO: 14.

10. The antibody or antigen-binding fragment of claim 1, wherein the VH region consists of the amino acid sequence of SEQ ID NO: 10 and the VL region consists of the amino acid sequence of SEQ ID NO: 12.

11. The antibody or antigen-binding fragment of claim 1, wherein the VH region consists of the amino acid sequence of SEQ ID NO: 10 and the VL region consists of the amino acid sequence of SEQ ID NO: 13.

12. The antibody or antigen-binding fragment of claim 1, wherein the VH region consists of the amino acid sequence of SEQ ID NO: 10 and the VL regions consists of the amino acid sequence of SEQ ID NO: 14.

13. The antibody or antigen-binding fragment of claim 1, wherein the VH region consists of the amino acid sequence of SEQ ID NO: 11 and the VL region consists of the amino acid sequence of SEQ ID NO: 12.

14. The antibody or antigen-binding fragment of claim 1, wherein the VH region consists of the amino acid sequence of SEQ ID NO: 11 and the VL region consists of the amino acid sequence of SEQ ID NO: 13.

15. The antibody or antigen-binding fragment of claim 1, wherein the VH region consists of the amino acid sequence of SEQ ID NO: 11 and the VL region consists of the amino acid sequence of SEQ ID NO: 14.

16. The antibody or antigen-binding fragment of claim 1, wherein the VH region consists of the amino acid sequence of SEQ ID NO: 43 and VL region consists of a sequence selected from the group consisting of SEQ ID NO: 12, SEQ ID NO: 13 and SEQ ID NO: 14.

17. The antibody or antigen-binding fragment of claim 1, wherein the VH region consists of the amino acid sequence of SEQ ID NO: 44 and VL region consists of a sequence selected from the group consisting of SEQ ID NO: 12, SEQ ID NO: 13 and SEQ ID NO: 14.

18. The antibody or antigen-binding fragment of claim 1, wherein the VH region consists of the amino acid sequence of SEQ ID NO: 45 and VL region consists of a sequence selected from the group consisting of SEQ ID NO: 12, SEQ ID NO: 13 and SEQ ID NO: 14.

19. The antibody or antigen-binding fragment of claim 1, wherein the VH region consists of the amino acid sequence of SEQ ID NO: 42 and VL region consists of a sequence selected from the group consisting of SEQ ID NO: 12, SEQ ID NO: 13 and SEQ ID NO: 14.

20. The antibody or antigen-binding fragment of claim 1, wherein the isotype of the constant region is IgG1, IgG2, IgG3, or IgG4.

21. The antibody or antigen-binding fragment of claim 20, wherein the isotype of the IgG constant region is IgG1.

22. The antibody or antigen-binding fragment of claim 20, wherein the isotype of the IgG constant region is IgG4.

23. The antibody or antigen-binding fragment of claim 1 having a heavy chain immunoglobulin constant domain selected from the group consisting of a human IgG1 constant domain and a human IgG4 constant domain.

24. The antibody or antigen-binding fragment of claim 1 having a human Ig kappa constant domain.

25. The antibody or antigen-binding fragment of claim 1, wherein the antibody is aglycosylated.

26. The antibody or antigen-binding fragment of claim 1 having a human IgG1 constant domain that is aglycosylated by replacing the amino acid corresponding to asparagine (Asn) 297 of the constant region heavy chain with an alternative amino acid residue.

27. The antibody or antigen-binding fragment of claim 26, wherein the Asn 297 is replaced with glutamine, alanine, histidine or glycine.

28. The antibody or antigen-binding fragment of claim 27, wherein the Asn 297 is replaced with glutamine.

29. The antibody or antigen-binding fragment of claim 1, wherein the heavy chain immunoglobulin constant domain is a human IgG4 constant domain wherein serine 228 is replaced with proline.

30. The antibody or antigen-binding fragment of claim 1, which is a scFv, diabody, Fab, minibody or scFv-Fc.

31. A pharmaceutical composition comprising a pharmaceutically acceptable carrier and an antibody or antigen-binding fragment of claim 1.

32. A method of treating an inflammatory disease or disorder comprising administering to a subject an effective amount of the antibody or antigen-binding fragment of claim 1.

33. The method of claim 32, wherein the subject is a mammal.

34. The method of claim 33, wherein the mammal is a human.

35. The method of claim 32, wherein the ischemia-reperfusion results after myocardial infarction, stroke or a surgical procedure.

* * * * *

UNITED STATES PATENT AND TRADEMARK OFFICE
CERTIFICATE OF CORRECTION

| | |
|---|---|
| PATENT NO. | : 9,243,059 B2 |
| APPLICATION NO. | : 14/206316 |
| DATED | : January 26, 2016 |
| INVENTOR(S) | : Robyn J. Puro |

It is certified that error appears in the above-identified patent and that said Letters Patent is hereby corrected as shown below:

In the specification

AT COLUMN 1

At lines 14-16, delete "The invention was supported, in whole or in part, by Grant No. 10388353 from the National Institutes of Health. The Government has certain rights in the invention." and insert -- The invention was supported, in whole or in part, by Grant No. 5R44HL084821-03 from the National Institutes of Health. The Government has certain rights in the invention. --.

In the claims

AT COLUMN 52

At lines 36-37, In claim 32, delete "an inflammatory disease or disorder" and insert -- ischemia-reperfusion injury --.

Signed and Sealed this
Nineteenth Day of July, 2016

Michelle K. Lee
*Director of the United States Patent and Trademark Office*

SEQUENCE LISTING

```
<160> NUMBER OF SEQ ID NOS: 48

<210> SEQ ID NO 1
<211> LENGTH: 119
<212> TYPE: PRT
<213> ORGANISM: Mus sp.

<400> SEQUENCE: 1

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30
```

-continued

Tyr Met Tyr Trp Val Lys Gln Arg Pro Gly Gln Gly Leu Glu Trp Ile
          35                  40                  45

Gly Gly Ile Asn Pro Ser Asn Gly Gly Thr Asn Phe Asn Glu Lys Phe
        50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Trp Gly Tyr Asp Arg Glu Trp Phe Ala Tyr Trp Gly Gln Gly
            100                 105                 110

Thr Leu Val Thr Val Ser Ala
            115

<210> SEQ ID NO 2
<211> LENGTH: 113
<212> TYPE: PRT
<213> ORGANISM: Mus sp.

<400> SEQUENCE: 2

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Val Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

Arg

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Tyr Tyr Met Tyr
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ile Asn Pro Ser Asn Gly Gly Thr Asn Phe Asn Glu Lys Phe Lys
1               5                   10                  15

Ser

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Asp Arg Glu Trp Phe Ala Tyr
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Ser Lys Ser Leu Leu His Ser Asn Gly Asn Thr Tyr Leu Tyr
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Met Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Gln His Leu Glu Tyr Pro Phe Thr
1               5

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60
```

```
Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Tyr Met Tyr Trp Val Arg Gln Ala Pro Gly Gln Gly Leu Glu Trp Ile
             35                  40                  45

Gly Gly Ile Asn Pro Ser Asn Gly Gly Thr Asn Phe Asn Glu Lys Phe
     50                  55                  60

Lys Ser Lys Ala Thr Met Thr Val Asp Lys Ser Thr Ser Thr Ala Tyr
 65                  70                  75                  80

Met Glu Leu Arg Ser Leu Arg Ser Asp Asp Ser Ala Val Tyr Tyr Cys
                 85                  90                  95

Thr Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ser Tyr
                 20                  25                  30

Tyr Met Tyr Trp Val Arg Gln Ala Pro Gly Gln Gly Leu Glu Trp Ile
             35                  40                  45

Gly Gly Ile Asn Pro Ser Asn Gly Gly Thr Asn Phe Asn Glu Lys Phe
     50                  55                  60

Lys Ser Lys Ala Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Trp Gly Tyr Asp Arg Glu Trp Phe Ala Tyr Trp Gly Gln Gly
            100                 105                 110
```

```
Thr Leu Val Thr Val Ser Ser
        115

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Met Thr Gln Ser Pro Ala Thr Leu Ser Val Ser Pro Gly
1               5                   10                  15

Glu Arg Ala Thr Ile Ser Cys Arg Ser Ser Lys Ser Leu Leu His Ser
            20                  25                  30

Asn Gly Asn Thr Tyr Leu Tyr Trp Phe Gln Gln Lys Pro Gly Gln Pro
        35                  40                  45

Pro Lys Val Leu Ile Tyr Arg Met Ser Asn Leu Ala Ser Gly Val Pro
    50                  55                  60

Ala Arg Phe Ser Gly Ser Gly Ser Gly Thr Asp Phe Thr Leu Thr Ile
65                  70                  75                  80

Ser Ser Val Glu Pro Glu Asp Phe Ala Thr Tyr Tyr Cys Met Gln His
                85                  90                  95

Leu Glu Tyr Pro Phe Thr Phe Gly Gly Gly Thr Lys Leu Glu Ile Lys
            100                 105                 110

Arg

<210> SEQ ID NO 13
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg

<210> SEQ ID NO 14
<211> LENGTH: 113
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 14

Asp Ile Val Met Thr Gln Thr Pro Leu Ser Leu Ser Tyr Thr Pro Gly
1               5                   10                  15

Gln Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

Arg

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr
            20                  25                  30

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Val Lys Gln Ala Pro Gly Gln Gly Leu Glu Trp Ile Gly
1               5                   10

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Ala Thr Leu Thr Val Asp Lys Ser Ala Ser Thr Ala Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 18
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 18

Trp Gly Gln Gly Thr Leu Val Thr Val Ser Ser
1               5                   10

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Val Arg Gln Ala Pro Gly Gln Gly Leu Glu Trp Ile Gly
1               5                   10

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Ala Thr Met Thr Val Asp Lys Ser Thr Ser Thr Ala Tyr Met Glu
1               5                   10                  15

Leu Arg Ser Leu Arg Ser Asp Asp Ser Ala Val Tyr Tyr Cys Thr Arg
            20                  25                  30

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Gly Gln Gly Thr Leu Val Thr Val Ser Ser
1               5                   10

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
                         polypeptide

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr
            20                  25                  30

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Val Arg Gln Ala Pro Gly Gln Gly Leu Glu Trp Ile Gly
1               5                   10

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Lys Ala Thr Ile Thr Val Asp Lys Ser Thr Ser Thr Ala Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Gly Gln Gly Thr Leu Val Thr Val Ser Ser
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ile Val Met Thr Gln Ser Pro Ala Thr Leu Ser Val Ser Pro Gly
1               5                   10                  15

Glu Arg Ala Thr Ile Ser Cys
            20

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 28

Trp Phe Gln Gln Lys Pro Gly Gln Pro Pro Lys Val Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Val Pro Ala Arg Phe Ser Gly Ser Gly Ser Gly Thr Asp Phe Thr
1               5                   10                  15

Leu Thr Ile Ser Ser Val Glu Pro Glu Asp Phe Ala Thr Tyr Tyr Cys
            20                  25                  30

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Gly Gly Gly Thr Lys Leu Glu Ile Lys Arg
1               5                   10

<210> SEQ ID NO 31
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Phe Leu Gln Lys Pro Gly Gln Ser Pro Gln Leu Leu Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30
```

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Phe Gly Gln Gly Thr Lys Leu Glu Ile Lys Arg
1               5                   10
```

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Asp Ile Val Met Thr Gln Thr Pro Leu Ser Leu Ser Tyr Thr Pro Gly
1               5                   10                  15

Gln Pro Ala Ser Ile Ser Cys
            20
```

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Trp Phe Leu Gln Lys Pro Gly Gln Ser Pro Gln Leu Leu Ile Tyr
1               5                   10                  15
```

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30
```

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Phe Gly Gln Gly Thr Lys Leu Glu Ile Lys Arg
1               5                   10

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Lys Ala Thr Leu Thr Val Asp Lys Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Lys Ala Thr Met Thr Val Asp Lys Ser Thr Ser Thr Ala Tyr Met Glu
1               5                   10                  15

Leu Arg Ser Leu Arg Ser Asp Asp Ser Ala Val Tyr Tyr Cys Ala Arg
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Lys Ala Thr Ile Thr Val Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Gly Arg Val Thr Ile Thr Arg Asp Lys Ser Thr Ser Thr Ala Tyr
```

```
                65                  70                  75                  80
Met Glu Leu Arg Ser Leu Arg Ser Glu Asp Ser Ala Val Tyr Tyr Cys
                    85                  90                  95

Ala Arg Trp Gly Tyr Asp Arg Glu Trp Phe Ala Tyr Trp Gly Gln Gly
                100                 105                 110

Thr Leu Val Thr Val Ser Ser
        115

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
                20                  25                  30

Tyr Met Tyr Trp Val Lys Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Trp Gly Tyr Asp Arg Glu Trp Phe Ala Tyr Trp Gly Gln Gly
                100                 105                 110

Thr Leu Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Lys Ser Lys Ala Thr Met Thr Val Asp Lys Ser Thr Ser Thr Ala Tyr
65                  70                  75                  80

Met Glu Leu Arg Ser Leu Arg Ser Asp Asp Ser Ala Val Tyr Tyr Cys
                    85                  90                  95

Ala Arg Trp Gly Tyr Asp Arg Glu Trp Phe Ala Tyr Trp Gly Gln Gly
                100                 105                 110

Thr Leu Val Thr Val Ser Ser
```

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Lys Ser Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 46
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Ser Leu Leu His Ser
                20                  25                  30

Asn Gly Asn Thr Tyr Leu Tyr Trp Tyr Gln Gln Lys Pro Gly Gln Ala
            35                  40                  45

Pro Arg Leu Leu Ile Tyr Arg Met Ser Asn Arg Ala Thr Gly Ile Pro
        50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 47

Leu Met Lys Asn Met Asp Pro Leu Asn Asp Asn Val
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Met Lys Asn Met Asp Pro Leu Asn Asp Asn Ile
1               5                   10
```